(12) United States Patent
Che et al.

(10) Patent No.: US 7,125,987 B2
(45) Date of Patent: Oct. 24, 2006

(54) PROCESS FOR THE PREPARATION OF OXCARBAZEPINE AND RELATED INTERMEDIATES

(75) Inventors: Daqing Che, Brantford (CA); Nadia Corelli-Rennie, Hamilton (CA); Bhaskar Reddy Guntoori, Brantford (CA); Jodi Faught, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 11/153,370

(22) Filed: Jun. 16, 2005

(65) Prior Publication Data

US 2005/0282797 A1    Dec. 22, 2005

(30) Foreign Application Priority Data

Jun. 18, 2004    (CA)  .................................. 2471666

(51) Int. Cl.
C07D 223/22    (2006.01)
(52) U.S. Cl. ...................................... 540/589
(58) Field of Classification Search ................ 540/589
See application file for complete search history.

(56) References Cited

U.S. PATENT DOCUMENTS

| 3,642,775 A | 2/1972 | Schindler et al. ........... 260/239 |
| 4,579,683 A | 4/1986 | Aufderhaar .................. 260/239 |
| 5,658,900 A | 8/1997 | Boireau et al. .............. 514/217 |
| 5,808,058 A | 9/1998 | Milanese ..................... 540/588 |
| 6,670,472 B1 | 12/2003 | Ansari et al. ............... 540/589 |

FOREIGN PATENT DOCUMENTS

| CA | 1112241 | 11/1981 | ............ 260/241.15 |
| EP | 028 028 B1 | 10/1980 | |
| WO | 94/20110 | 9/1994 | |
| WO | 05/066133 | 7/2005 | |

OTHER PUBLICATIONS

Lohse et al. (Tetrahedron Letters 42 (2001), 385-389.*

* cited by examiner

*Primary Examiner*—Bruck Kifle
(74) *Attorney, Agent, or Firm*—Marcelo K. Sarkis; Ivor M. Hughes; Neil H. Hughes

(57) ABSTRACT

A process for preparing Oxcarbazepine III

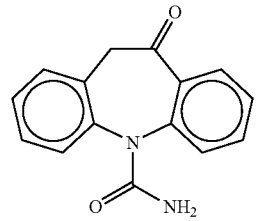

comprising:
a) reacting oximinostilbene IV

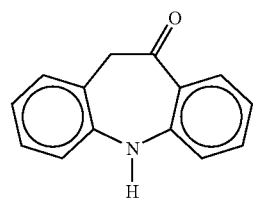

with chlorosulfonyl isocyanate in an inert organic solvent and isolating compound V

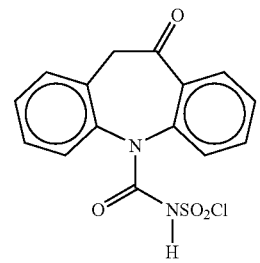

b) hydrolyzing compound V to form crude Oxcarbazepine III

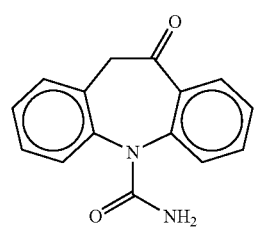

c) purifying oxcarbazepine.

37 Claims, No Drawings

PROCESS FOR THE PREPARATION OF OXCARBAZEPINE AND RELATED INTERMEDIATES

FIELD OF INVENTION

The present invention relates to an improved process for making oxcarbazepine (10-oxo-10,11-dihydro-5H-dibenz[b,f]azepine-5-carboxamide) starting from 10-methoxy-5H-dibenz[b,f]azepine (10-methoxyiminostilbene).

BACKGROUND OF THE INVENTION

Oxcarbazepine, a more tolerable alternative to the popular anticonvulsant drug carbamazepine, is used to treat epilepsy and has been proposed for use in the treatment of psychosomatic diseases and trigeminal neuralgia as described in U.S. Pat. No. 3,642,775. It has also been proposed for use in the treatment of Parkinsonian syndromes as described in U.S. Pat. No. 5,658,900, and AIDS-related neural disorders as described in WO 94/20110.

Several different routes for the preparation of oxcarbazepine are described in prior art documents such as: U.S. Pat. No. 3,642,775; U.S. Pat. No. 4,579,683; CA 1,112,241 and EP 028 028. In addition to being low yielding, these routes also hold the disadvantage of either starting with the costly raw material carbamazepine or they require the use of highly toxic reagents (i.e phosgene or cyanogen chloride) and are therefore impractical when transiting to commercial scale.

Processes better suited for large-scale production are claimed in U.S. Pat. No. 5,808,058 and U.S. Pat. No. 6,670,472. The process disclosed in U.S. Pat. No. 5,808,058 is depicted in Scheme 1. It begins with the carbamoylation of the readily available starting material 10-methoxyiminostilbene (10-methoxy-5H-dibenz[b,f]azepine) I, to give 10-methoxycarbamazepine II. This is achieved using an alkali metal cyanate like sodium cyanate and a relatively strong organic or inorganic acid, preferably acetic acid. The carbamoylation is then followed by hydrolysis of the enol-ether group under mildly acidic aqueous conditions to furnish oxcarbazepine III. Unfortunately, under the above carbamoylation conditions, a concomitant reaction, hydrolysis of the enol-ether group of 10-methoxyiminostilbene to the corresponding ketone, 5,11-dihydro-10H-dibenz[b,f]azepine-10-one (oximinostilbene) IV, also occurs. Once formed, IV will not undergo further conversion to oxcarbazepine in the presence of the metal cyanate and acid. Consequently, a mixture of products and related impurities are produced which requires a tedious and uneconomical purification procedure which results in low yields (45% to 65%) of final oxcarbazepine. Also, the purity of the final product is not reported.

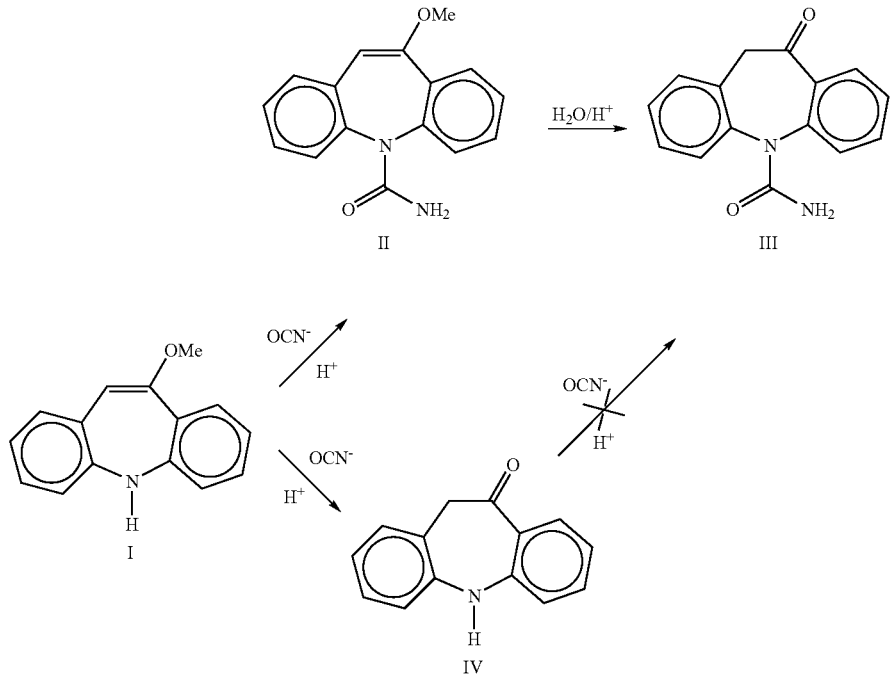

Scheme 1

An alternative process involving a condensation reaction with chlorosulfonyl isocyanate is disclosed in the same patent. As illustrated in Scheme 2, the enol-ether moiety of 10-methoxyiminostilbene I is first hydrolyzed in dilute acid to produce oximinostilbene IV, which is isolated and reacted with chlorosulfonyl isocyanate in a halogenated solvent to provide intermediate V. The chlorosulfonyl group of V is then hydrolyzed by the addition of water in the same pot to give oxcarbazepine III. There are drawbacks to this process. Firstly, the preparation of oximinostilbene IV requires harsh (reflux) conditions, and involves a tedious work-up procedure. Secondly, the reaction with chlorosulfonyl isocyanate and the subsequent hydrolysis also requires a relatively complicated isolation procedure giving a very low overall yield of only 34% oxcarbazepine. The purity of the final product is not reported.

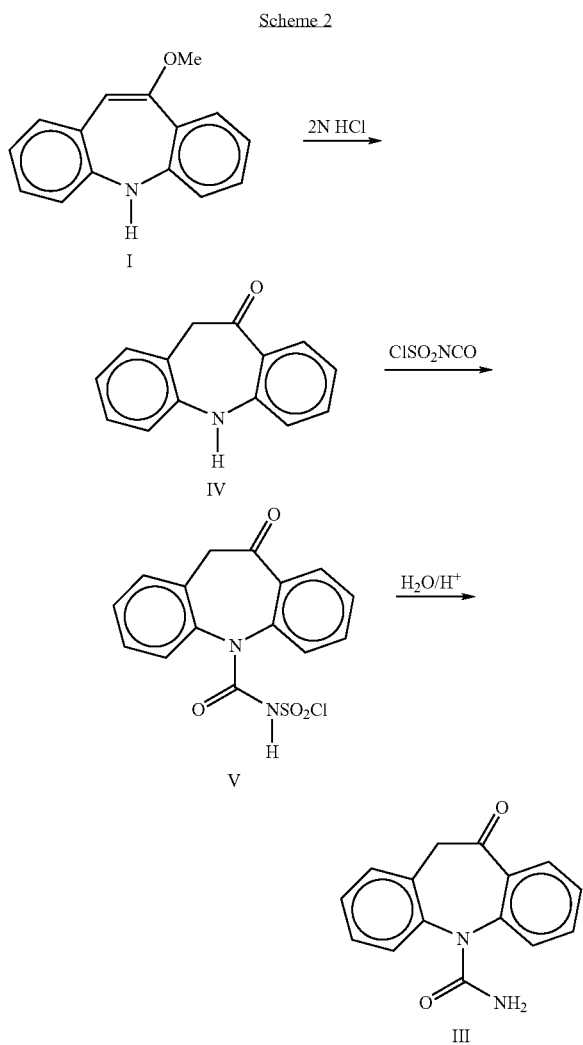

Scheme 2

U.S. Pat. No. 6,670,472 discloses a more efficient process derived from U.S. Pat. No. 5,808,058 which involves reacting 10-methoxyiminostilbene I with a metal cyanate in the presence of a weak, recyclable, organic acid (which contributes HOCN). Preferably the weak organic acid is benzoic acid, that is relatively insoluble in the solvent, preferably toluene. This results in an improved selectivity for the desired carbamoylation reaction relative to the hydrolysis of the enol-ether. This step is then followed by hydrolysis of the enol-ether group with a dilute acid, like hydrochloric acid, in a biphasic solvent system (preferably toluene/water) such that the product is insoluble in both phases but the impurities are soluble in at least one of the phases. The product is then isolated by filtration and purified once by recrystallization. Although this process offers some advantages, the yield is sacrificed, being only 49% even under optimized conditions.

The prior art processes described above, although better than those listed earlier, still suffer from serious drawbacks including complicated isolation procedures, inefficiency and/or low yields.

It is therefore an object of this invention to overcome the deficiencies of the prior art and provide a higher yielding, cost-effective, and scalable process for the commercial production of highly pure oxcarbazepine III.

It is a further object of this invention to provide a process where oxcarbazepine intermediate IV is made in a higher yielding, cost-effective, and scalable process for the commercial production.

Further objects will be realized by those skilled in the art from the following summary of the invention and detailed description of embodiments of the invention.

SUMMARY OF THE INVENTION

Surprisingly and according to one aspect of the invention, it has been found that oxcarbazepine intermediate IV can be prepared by a highly advantageous method that, relative to the processes in the prior art, is straightforward and high yielding. Moreover, only mild reaction conditions are required and the isolation procedure is facile thereby furnishing a product which meets the high purity specifications found in the pharmaceutical industry. We have found according to the one aspect of the invention that the enol-ether group of 10-methoxyiminostilbene I can be quickly hydrolyzed to the corresponding ketone IV in the presence of a catalytic amount of a dilute mineral acid such as sulfuric, nitric, or hydrochloric acid. Preferably the acid is in a concentration of 5–50%, more preferably the concentration is 5–15%. Most preferably the acid is hydrochloric acid.

The hydrolysis is preferably conducted in an organic solvent, preferably the solvent is a water-miscible ketone solvent such as acetone, a water-miscible ether such as tetrahydrofuran or a $C_1$ to $C_6$ alcohol. Most preferably the solvent is acetone. The hydrolysis is conducted at 10° C.–40° C., preferably at 15° C.–30° C. In one embodiment the solution is stirred for more than one hour and then the product can be simply precipitated by the addition of water, and easily isolated by filtration giving oximinostilbene IV in an almost quantitative yield and very high purity. Additional purifications are not required.

According to another aspect of the invention, it has been found that oxcarbazepine III can be prepared in high yield and purity from oximinostilbene IV. Intermediate IV is reacted rapidly in an almost quantitative yield with preferably about 1–1.5 equivalents (preferably about 1.05 equivalents) of chlorosulfonyl isocyanate, at preferably a relatively low temperature between about 0° C.–about 10° C. (preferably between about 0° C.–about 5° C.), in preferably an inert organic solvent such as a $C_1$ to $C_3$ chlorinated hydrocarbon such as dichloromethane or chloroform, a $C_6$ to $C_9$ aromatic solvent such as toluene, or a $C_2$ to $C_5$ nitrile solvent such as acetonitrile to provide Intermediate V. Most preferably the solvent is acetonitrile.

Intermediate V is isolated by for example, filtration and then hydrolyzed (preferably at a temperature less than about 60° C., more preferably below about 20° C.) to oxcarbazepine with water or aqueous acid or base. Preferably intermediate V is hydrolyzed by water in an organic solvent such as a $C_1$ to $C_3$ chlorinated hydrocarbon such as dichloromethane or chloroform, a $C_3$ to $C_6$ ketone solvent such as acetone or methyl isobutyl ketone, a $C_2$ to $C_7$ ester solvent such as ethyl acetate or a $C_1$, to $C_6$ acid such as acetic acid to provide oxcarbazepine III. Most preferably the hydrolysis is conducted in acetic acid.

The isolation of intermediate V prior to hydrolysis permits for easier isolation of the final product.

Preferably, the product is precipitated by the addition of water or an organic solvent such as a $C_3$ to $C_6$ ketone solvent such as acetone or methyl isobutyl ketone, a $C_1$ to $C_6$ alcohol solvent such as ethanol or isopropanol, or a $C_2$ to $C_7$ ester solvent such as ethyl acetate and then filtered and purified further in an organic solvent such as a $C_1$ to $C_6$ alcohol solvent such as ethanol or isopropanol, a $C_3$ to $C_6$ ketone solvent such as methyl isobutyl ketone or acetone or mixtures thereof or mixtures of these solvents with water to give oxcarbazepine III in high yield and purity. The purification may be conducted at a range of temperatures for example between about 10° C. and preferably between about room temperature to reflux temperature.

DETAILED DESCRIPTION OF EMBODIMENTS OF THE INVENTION

EXAMPLE 1

Preparation of 5,11-Dihydro-10H-dibenz[b,f]azepine-10-one (Oximinostilbene) IV

A 2-L, three-necked flask equipped with a mechanical stirrer, thermometer and nitrogen inlet was charged with 10-methoxyiminostilbene I (110.0 g, 0.49 mol) and 330 mL acetone. A 10% solution of hydrochloric acid (28.6 g, 0.08 mol) was then added. The reaction mixture was stirred at ambient temperature for 1–1.5 hours until reaction completion. The product was precipitated by the addition of 660 mL of deionized water, and the resulting suspension was stirred for 3–4 hours. The suspension was filtered and washed with water. After drying, oximinostilbene (99.92 g, 97%) was obtained as a bright yellow solid having a purity of 99% by HPLC.

$^1$H NMR (CDCl$_3$, d): 3.80, 6.87, 7.04–7.15, 7.22–7.24, 7.32–7.37, 8.04 ppm.

EXAMPLE 2

Preparation of 10-Oxo-10,11-dihydro-5H-dibenz[b,f]azepin-5-carboxamide III

A 1-L, three-necked flask equipped with a thermometer, nitrogen inlet, mechanical stirrer and addition funnel, was charged with oximinostilbene IV (prepared above) followed by 400 mL dichloromethane. The suspension was cooled to 0–5° C. and a solution of chlorosulfonyl isocyanate (71.7 g, 0.50 mol) in 200 mL dichloromethane was added dropwise, maintaining the internal temperature at 0–10° C. Following the addition, the reaction mixture was maintained at 0–5° C. until reaction completion. The cold suspension was then filtered and washed giving oxcarbazepine intermediate V (163 g, 97%). The damp solid was suspended in 300 ml glacial acetic acid and cooled to 10–15° C. To the suspension was added 188 mL cold water, portionwise, maintaining the IT<20° C. The mixture was maintained at 15–25° C. for 0.5–1.0 h until reaction completion. The suspension was concentrated to 200–300 ml and 700 mL isopropanol was added to precipitate the product. The suspension was then filtered and washed. The damp cake was purified in an isopropanol:water mixture to furnish oxcarbazepine as a white to off-white solid (101.27 g, 84%, purity of 99.5% by HPLC).

$^1$H NMR (DMSO, d): 4.06, 6.19, 7.30–7.39, 7.44–7.51, 7.63, 7.91 ppm.

While the foregoing provides a detailed description of a preferred embodiment of the invention, it is to be understood that this description is illustrative only of the invention and should not be interpreted in a limiting sense. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for preparing Oxcarbazepine III

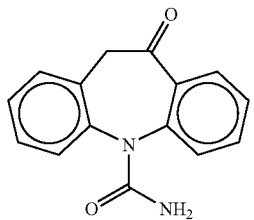

comprising:
a) reacting oximinostilbene IV

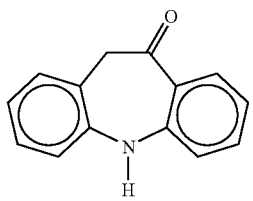

with chlorosulfonyl isocyanate in an inert organic solvent and isolating compound V

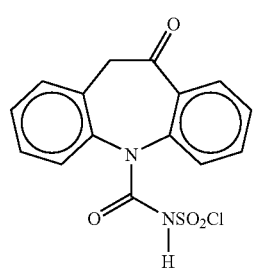

b) hydrolyzing compound V to form crude Oxcarbazepine III

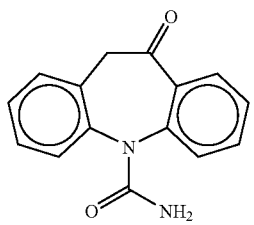

c) purifying oxcarbazepine.

2. The process of claim 1 wherein the said inert organic solvent of step (a) is selected from a group consisting of: a $C_1$ to $C_3$ chlorinated solvent, a $C_6$ to $C_9$ aromatic solvent, a $C_2$ to $C_5$ nitrite solvent and mixtures thereof.

3. The process of claim 2 wherein the said inert organic solvent of step (a) is selected from the group consisting of: dichloromethane, chloroform, toluene, acetontrile and mixtures thereof.

4. The process of claim 1 wherein the chlorosulfonyl isocyanate used ranges from about 1 to 1.5 molar equivalents of the Oximinostilbene IV.

5. The process of claim 4 wherein the chlorosulfonyl isocyanate used ranges from about 1 to 1.2 molar equivalents of the Oximinostilbene IV.

6. The process of claim 5 wherein the chlorosulfonyl isocyanate is used in 1.05 molar equivalents to the Oximinostilbene IV.

7. The process of claim 1 wherein the hydrolysis of step (b) is conducted in the presence of a $C_1$ to $C_6$ organic acid.

8. The process of claim 7 wherein the hydrolysis of step (b) is conducted in the presence of acetic acid.

9. The process of claim 1 wherein an organic solvent is used in step (c) and the organic solvent is selected from a $C_2$ to $C_7$ ester solvent, a $C_1$ to $C_6$ alcohol solvent and mixtures thereof with water.

10. The process of claim 1 wherein step (a) is carried out at a temperature of between about 0° C. to about 10° C.

11. The process of claim 10 wherein step (a) is carried out at a temperature of between about 0° C. to about 5° C.

12. The process of claim 1 wherein in step (b) the hydrolysis is conducted below about 60° C.

13. The process of claim 12 wherein the hydrolysis step in step (b) is conducted below about 20° C.

14. The process of claim 1 wherein the purification in step (c) is conducted at between about 10° C. to reflux temperature.

15. A process for preparing compound IV

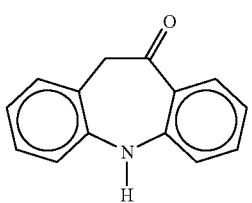

IV comprising hydrolysis of compound I

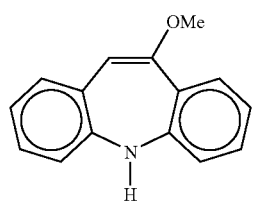

I with an aqueous inorganic acid in a water-miscible organic solvent.

16. The process of claim 15 wherein the inorganic acid is selected from the group consisting of: sulfuric, hydrochloric, and nitric acid.

17. The process of claim 15 wherein the concentration of inorganic acid ranges from between about 5 to about 50%.

18. The process of claim 17 wherein the concentration of inorganic acid ranges from between about 5 to about 15%.

19. The process of any one of claim 15 wherein the inorganic acid added ranges from about 0.1 to about 1 molar equivalents of compound IV.

20. The process of claim 15 wherein the inorganic acid added ranges from about 0.1 to about 0.5 molar equivalents of compound IV.

21. The process of claim 20 wherein the inorganic acid added ranges from about 0.1 to about 0.2 molar equivalents of compound IV.

22. The process of claim 15 wherein the said organic solvent is selected from a $C_2$ to $C_7$ ketone solvent, a $C_2$ to $C_5$ nitrile solvent, a $C_1$ to $C_6$ alcohol solvent and mixtures thereof.

23. The process of claim 15 wherein the said organic solvent is selected from acetone, acetonitrile, methanol, ethanol, isopropanol and mixtures thereof.

24. The process of claim 15 wherein the hydrolysis is conducted at about 10 to about 40° C.

25. The process of claim 24 wherein the hydrolysis is conducted at about 15 to about 30° C.

26. The process of claim 1 wherein the purified oxcarbazepine has of purity >99.5%.

27. The process of claim 1 wherein compound IV is prepared by the process of claim 15.

28. The process of claim 1 wherein compound IV is prepared by the process of claim 16.

29. The process of claim 1 wherein compound IV is prepared by the process of claim 17.

30. The process of claim 1 wherein compound IV is prepared by the process of claim 18.

31. The process of claim 1 wherein compound IV is prepared by the process of claim 19.

32. The process of claim 1 wherein compound IV is prepared by the process of claim 20.

33. The process of claim 1 wherein compound IV is prepared by the process of claim 21.

34. The process of claim 1 wherein compound IV is prepared by the process of claim 22.

35. The process of claim 1 wherein compound IV is prepared by the process of claim 23.

36. The process of claim 1 wherein compound IV is prepared by the process of claim 24.

37. The process of claim 1 wherein compound IV is prepared by the process of claim 25.

* * * * *

UNITED STATES PATENT AND TRADEMARK OFFICE
CERTIFICATE OF CORRECTION

| | | |
|---|---|---|
| PATENT NO. | : 7,125,987 B2 | Page 1 of 1 |
| APPLICATION NO. | : 11/153370 | |
| DATED | : October 24, 2006 | |
| INVENTOR(S) | : Daqing Che et al. | |

It is certified that error appears in the above-identified patent and that said Letters Patent is hereby corrected as shown below:

TITLE Page, Item (75) INVENTORS:

The name of the inventor "Jodi Faught" should be changed to -- Jody Faught --.

Signed and Sealed this

Sixteenth Day of January, 2007

JON W. DUDAS
*Director of the United States Patent and Trademark Office*